US006858382B2

(12) United States Patent
Brent et al.

(10) Patent No.: US 6,858,382 B2
(45) Date of Patent: *Feb. 22, 2005

(54) DETECTION SYSTEMS FOR REGISTERING PROTEIN INTERACTIONS AND FUNCTIONAL RELATIONSHIPS

(75) Inventors: Roger Brent, Berkeley, CA (US); C. Wilson Xu, New York, NY (US); Andrew R. Mendelsohn, Sausalito, CA (US); Walter L. Lok, San Francisco, CA (US)

(73) Assignee: The General Hospital Corporation, Boston, MA (US)

( * ) Notice: Subject to any disclaimer, the term of this patent is extended or adjusted under 35 U.S.C. 154(b) by 14 days.

This patent is subject to a terminal disclaimer.

(21) Appl. No.: 09/757,309

(22) Filed: Jan. 9, 2001

(65) Prior Publication Data

US 2002/0072088 A1 Jun. 13, 2002

Related U.S. Application Data

(63) Continuation of application No. 09/189,653, filed on Nov. 10, 1998, now Pat. No. 6,171,792.
(60) Provisional application No. 60/065,273, filed on Nov. 10, 1997.

(51) Int. Cl.[7] .............................. C12Q 1/00; C12Q 1/68; C12P 21/06; G01N 33/566
(52) U.S. Cl. .............................. 435/4; 435/6; 435/68.1; 435/69.1; 436/501
(58) Field of Search .............................. 435/4, 6, 68.1, 435/69.1; 436/501

(56) References Cited

U.S. PATENT DOCUMENTS 4,833,080 A     5/1989   Brent et al.
4,980,281 A    12/1990   Housey
5,270,181 A    12/1993   McCoy et al.
5,283,173 A     2/1994   Fields et al.
5,525,490 A     6/1996   Erickson et al.
5,589,362 A    12/1996   Bujard et al.
5,965,368 A  * 10/1999   Vidal et al. .................... 435/6

FOREIGN PATENT DOCUMENTS

WO     WO96/32503     10/1996
WO     WO 99/14319     3/1999

OTHER PUBLICATIONS

Berger et al., *Cell* 70:251–265 (1992).
Bishop, *Science* 235:305–311 (1987).
Brent et al., *Cell* 43:729–736 (1985).
Brent et al., *Nature* 312:612–615, (1984).
Broach et al., *Gene* 8:121–123, (1979).
Celenza et al., *Mol. Cell Biol*. 9:5034–5044 (1989).
Celenza et al., *Mol. Cell Biol*. 9:5045–5054 (1989).
Celenza et al., *Science* 233:1175–1180 (1986).
Chakraborty et al., *J. Biol. Chem.* 267:17498–17501 (1992).
Chien et al., *Proc. Natl. Acad. Sci. USA* 88:9578–9582 (1991).
Curran et al., *Cell* 55:395–397 (1988).
Dalton and Treisman, *Cell* 68:597–612 (1992).
Dang et al., *Mol. Cell Bio.* 11:954–962 (1991).
Draetta, *Trends in Biochem. Sci.* 15:378–382 (1990).
Fearon et al., *Proc. Natl. Acad. Sci. USA* 89:7958–7962 (1992).
Fields and Song, *Nature* 340:245–246 (1989).

(List continued on next page.)

*Primary Examiner*—Kenneth R. Horlick
*Assistant Examiner*—Teresa Strzelecka
(74) *Attorney, Agent, or Firm*—Clark & Elbing LLP

(57) ABSTRACT

Disclosed herein are methods for detecting complex protein interactions and protein functional relationships, and reagents for carrying out those methods.

16 Claims, 6 Drawing Sheets

OTHER PUBLICATIONS

Fields et al., *Trends in Genetics* 10:286–292 (1994).
Finkel et al., *The Journal of Biological Chemistry* 268:5–8 (1993).
Furey et al., *Science* 231:704–707 (1986).
Gill et al., *Nature* 334:721–724 (1988).
Gill et al., *Cell* 51:121–126 (1987).
Giniger et al., *Cell* 40:767–774 (1985).
Goff et al., *Genes & Development* 5:864–875 (1992).
Gyuris et al., *Cell* 75:791–803 (1993).
Hadwiger et al., *Proc. Natl. Acad. Sci. USA* 86:6255–6259 (1989).
Hansen et al., *Cell* 53:172–173 (1988).
Hardy et al., *Genes & Development* 6:801–814 (1992).
Hartley, "Cellular Interaction in Development, A Practical Approach," *IRL Press* (NY), pp. 153–179 (1994).
Harper et al., *Cell* 75:805–816 (1993).
Hope et al., *Cell* 46:885–894 (1986).
Hope et al., *Nature* 333:635–640 (1988).
Hu et al., *Science* 250:1400–1403 (1990).
Johnston, *Microbiological Reviews* 51:458–476 (1987).
Keegan et al., *Science* 231:699–704 (1986).
Koff et al., *Cell* 66:1217–1228 (1991).
Kumar et al., *Cell* 51:941–951 (1987).
Laughon et al., *Mol. Cell Bio.* 4:260–267 (1984).
LaVaille et al., *Bio/Technology* 11:187–193 (1993).
Lech et al., *Cell* 52:179–184 (1988).
LeDouarin et al., *Nucleic Acids Research* 23:876–878 (1995).
Levine et al., *Cell* 59:405–408 (1989).
Ma et al., *Cell* 55:443–446 (1988).
Ma et al., *Cell* 51:113–119 (1987).
Ma et al., *Cell* 48:847–853 (1987).
Martin et al., *Mol. Cell Bio.* 10:1908–1914 (1990).
McKnight et al., *Proc. Natl. Acad. Sci. USA* 84:7061–7065 (1987).
Meyerson et al., *The EMBO Journal* 11:2909–2917 (1992).
Pines et al., *Cell* 59:833–846 (1989).
Reddy et al., *Proc. Natl. Acad. Sci. USA* 80:2500–2504 (1983).
Richardson et al., *Cell* 59:1127–1133 (1989).
Richardson et al., *Genes & Development* 4:1332–1344 (1990).
Shih et al., *Proc. Natl. Acad. Sci. USA* 93:13896–13901 (1996).
Silver et al., *Proc. Natl. Acad. Sci. USA* 81:5951–5955 (1984).
Struhl, *Annu. Rev. Biochem* 58:1051–1077 (1989).
Struhl, *Nature* 332:649–650 (1988).
Thukral et al., *Mol. Cell Biol.* 9:2360–2369 (1989).
Touchette, *The Journal of NIH Research* 3:44–46 (1991).
Tsai et al., *Nature* 353:174–177 (1991).
Van Beveren et al., *Cell* 32:1241–1255 (1983).
Vidal et al., *Proc. Natl. Acad. Sci. USA* 93:10315–10320 (1996).
Wittekind et al., *Mol. Cell Bio.* 8:3997–4008 (1988).
Wittenberg et al., *Cell* 54:1061–1072 (1988).
Wittenberg et al., *Cell* 62:225–237 (1990).
Wittenberg et al., *Molecular and Cellular Biology* 9:4064–4068 (1989).
Xiong et al., *Cell* 65:691–699 (1991).
Xu et al., *Proc. Natl. Acad. Sci. USA* 94:12473–12478 (1997).
Yang et al., *Science* 257:680–682 (1992).
Zervos et al., *Cell* 72:223–232 (1993).
Brachmann et al., "Tag Games in Yeast: The Two–Hybrid System and Beyond," *Current Opinion in Biotechnology* 8:561–568 (1997).
Collas et al., "The Impact of Two–Hybrid and Related Methods on Biotechnology," *TIBTECH* 16 355–363 (1998).
Cormack et al., "Dampening of Bait Proteins in the Two–Hybrid System," *Analytical Biochemistry* 248:184–186 (1997).
Golling et al., "Drosophila Homologs of the Proto–Oncogene Product PEBP2/CBFβ Regulate the DNA–Binding Properties of Runt," *Molecular and Cellular Biology* 16:932–942 (1996).
Grossel et al., "A Yeast Two–Hybrid System for Discerning Differential Interactions Using Multiple Baits," *Nature Biotechnology* 17 1232–1233 (1999).
Jiang et al., "Glucose Regulates Protein Interactions Within the Yeast SNF1 Protein Kinase Complex," *Genes & Development* 10:3105–3115 (1996).
Leanna et al., The Reverse Two–Hybrid System: A Genetic Scheme for Selection Against Specific Protein/Protein Interactions,' *Nucleic Acids Research* 24:3341–3347 (1996).
Osborne et al., "The Yeast Tribrid System ——Genetic Detection of trans–Phosphorylated ITAM–SH2–Interactions." *Biotechnology* 13, 1474–1478 (1995).
Shrivastava et al., "Inhibition of Transcriptional Regulator Yin–Yang–1 by Association with c–Myc," *Science* 262:1889–1892 (1993).
Tirode et al., "A Conditionally Expressed Third Partner Stabilizes or Prevents the Formation of a Transcriptional Activator in a Three–Hybrid System," *The Journal of Biological Chemistry* 272:22995–22999 (1997).
Zhao et al., "Analysis of Vitamin D Analog–Induced Heterodimerization of Vitamin D Receptor with Retinoid X Receptor Using the Yeast Two–Hybrid System." *Molecular Endocrinology* 11:366–378 (1997).

* cited by examiner

| Baits | Prey | Reporter | Reporter Output | | Logical Relationship |
|---|---|---|---|---|---|
| | | | X-Gal Glu / URA- Glu | X-Gal Gal / URA- Gal | |
| LexA-hSos1 | B42-Ras B42 | LexOp-LacZ | | | And |
| TetR-c-Raf1 | B42-Ras B42 | TetOp-URA3 | | | |
| LexA-Max | B42-c-Raf1 B42-Mxi1 | LexOp-LacZ | | | Ls1 |
| TetR-RasV12 | B42-c-Raf1 B42Mxi1 | TetOp-URA3 | | | Ls2 |
| LexA-RasV12 | B42-c-Raf1 B42-Cdc25 | LexOp-LacZ | | | Ls1 |
| TetR-RasA15 | B42-c-Raf1 B42-Cdc25 | TetOp-URA3 | | | Ls2 |

FIG. 2

| Cell | LacZ Output | β–Galactosidase Activity |
|------|-------------|--------------------------|
| 1    |             | 22.6 ± 3.3               |
| 2    |             | 7.4 ± 1.0                |
FIG. 3A
Cell 1
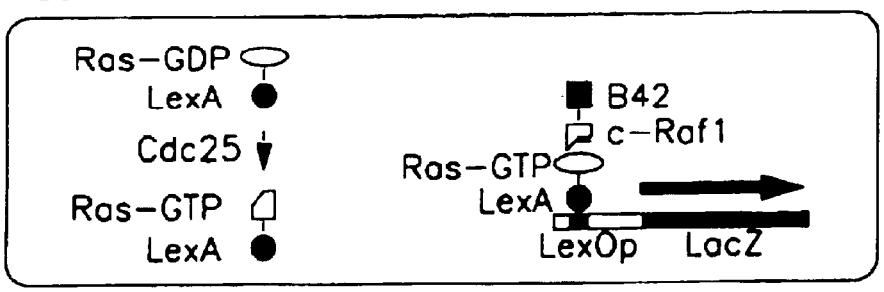
Cell 2
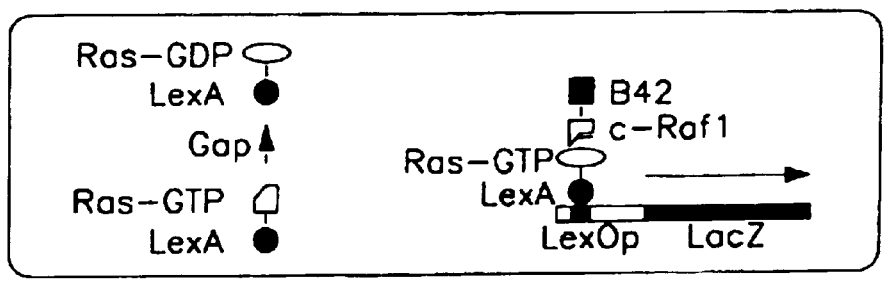
FIG. 3B
| Input Values | | LacZ Output |
|---|---|---|
| 1(B42-c-Raf1) | 0(GAP) | 0 |
| 1(B42-c-Raf1) | 1(Cdc25) | 1 |
FIG. 3C

SEQUENCE LISTING

<160> NUMBER OF SEQ ID NOS: 17

<210> SEQ ID NO 1
<211> LENGTH: 14
<212> TYPE: DNA
<213> ORGANISM: Saccharomyces cerevisiae

<400> SEQUENCE: 1
gatccgcggc cgcg                                                      14

<210> SEQ ID NO 2
<211> LENGTH: 41
<212> TYPE: DNA
<213> ORGANISM: Saccharomyces cerevisiae

<400> SEQUENCE: 2
aaaaggaaaa gcggccgctt agttttgctg gccgcatctt c                        41

<210> SEQ ID NO 3
<211> LENGTH: 32
<212> TYPE: DNA
<213> ORGANISM: Saccharomyces cerevisiae

<400> SEQUENCE: 3
cggaattctt tcgaaagcta catataagga ac                                  32

<210> SEQ ID NO 4
<211> LENGTH: 56
<212> TYPE: DNA
<213> ORGANISM: Escherichia coli

<400> SEQUENCE: 4
tcgagcactc cctatcagtg atagagaaaa cactccctat cagtgataga gaaaag        56

<210> SEQ ID NO 5
<211> LENGTH: 56
<212> TYPE: DNA
<213> ORGANISM: Escherichia coli

<400> SEQUENCE: 5
cgtgagggat agtcactatc tcttttgtga gggatagtca ctatctcttt tcagct        56

<210> SEQ ID NO 6
<211> LENGTH: 14
<212> TYPE: DNA
<213> ORGANISM: Saccharomyces cerevisiae

<400> SEQUENCE: 6
ggccgcggta ccgc                                                      14

<210> SEQ ID NO 7
<211> LENGTH: 29
<212> TYPE: DNA
<213> ORGANISM: Homo sapiens

<400> SEQUENCE: 7

-continued

```
gcctgaattc atgacggaat ataagctgg                              29

<210> SEQ ID NO 8
<211> LENGTH: 35
<212> TYPE: DNA
<213> ORGANISM: Homo sapiens

<400> SEQUENCE: 8
cccgaactcg agtcaggaga gcactgcctt gcagc                       35

<210> SEQ ID NO 9
<211> LENGTH: 25
<212> TYPE: DNA
<213> ORGANISM: Homo sapiens

<400> SEQUENCE: 9
gcctgaattc aaagcaggaa ctgtt                                  25

<210> SEQ ID NO 10
<211> LENGTH: 33
<212> TYPE: DNA
<213> ORGANISM: Homo sapiens

<400> SEQUENCE: 10
cccgaactcg agctatcgtg gttctatttc tag                         33

<210> SEQ ID NO 11
<211> LENGTH: 29
<212> TYPE: DNA
<213> ORGANISM: Saccharomyces cerevisiae

<400> SEQUENCE: 11
gcctgaattc atgtcttcgg tctcctcag                              29

<210> SEQ ID NO 12
<211> LENGTH: 33
<212> TYPE: DNA
<213> ORGANISM: Saccharomyces cerevisiae

<400> SEQUENCE: 12
cccgaactcg agttatcgaa ataacctaga agg                         33

<210> SEQ ID NO 13
<211> LENGTH: 31
<212> TYPE: DNA
<213> ORGANISM: Homo sapiens

<400> SEQUENCE: 13
gcctgaattc atgaagggt ggtatcacgg a                            31

<210> SEQ ID NO 14
<211> LENGTH: 35
<212> TYPE: DNA
<213> ORGANISM: Homo sapiens

<400> SEQUENCE: 14
cccgaactcg agctacttga catcattggt ttttg                       35

<210> SEQ ID NO 15
<211> LENGTH: 20
<212> TYPE: PRT
<213> ORGANISM: Homo sapiens

<400> SEQUENCE: 15
```

```
-continued

Asp Met Asp Trp Phe Phe Arg Phe Tyr Ala Ser Val Ser Arg Leu Phe
  1               5                   10                  15

Arg His Leu His
             20

<210> SEQ ID NO 16
<211> LENGTH: 20
<212> TYPE: PRT
<213> ORGANISM: Homo sapiens

<400> SEQUENCE: 16

Phe Trp Gln Ala Thr Leu Arg Leu Val Ser Asp Lys Leu Ile Leu Leu
  1               5                   10                  15

Tyr Pro Asp Pro
             20

<210> SEQ ID NO 17
<211> LENGTH: 16
<212> TYPE: DNA
<213> ORGANISM: Homo sapiens

<400> SEQUENCE: 17
ctagggccct agcatg                                                    16
```

DETECTION SYSTEMS FOR REGISTERING PROTEIN INTERACTIONS AND FUNCTIONAL RELATIONSHIPS

CROSS-REFERENCE TO RELATED APPLICATIONS

This application is a continuation of U.S. application Ser. No. 09/189,653, filed Nov. 10, 1998 (now U.S. Pat. No. 6,171,792), and U.S. Provisional Application No. 60/065,273, filed Nov. 10, 1997 (now abandoned).

BACKGROUND OF THE INVENTION

This invention relates to protein interaction detection systems.

Genetic analysis is a tool for understanding the protein networks that govern biological processes. The manipulations performed by geneticists (e.g., staging of temperature sensitive mutants, construction and analysis of double mutants, and generation and observation of F1 and F2 progeny) define relationships between genes. These abstract relationships between genes often reflect underlying biological realities. For example, the epistasis relation may suggest that one gene normally acts on another to cause a phenotype, the allelic specific suppression relation may suggest that two gene products physically interact (Hartman and Roth, *Adv. Genet.* 17:1–105 (1973); Jarvik and Botstein, *Proc. Natl. Acad. Sci. USA* 70:2046–50 (1973)), and the dependency relation may suggest that the action of one gene product precedes that of another in time (Hereford and Hartwell, *J. Mol. Biol.* 84:445–61 (1974)).

Information obtained from these genetic manipulations is typically of very high quality, but is often relatively difficult to acquire. The recent increase in the rate of identification of new coding sequences has renewed interest in global systematic methods to understand gene function. These methods include the "two hybrid" or "interaction trap" methods which have been developed to assay contact between a single bait and interacting proteins (Fields and Song, *Nature* 340:245–6 (1989); Chien et al., *Proc. Natl. Acad. Sci. USA* 88:9578–82 (1991); Gyuris et al., *Cell* 75:791–803 (1993); Durfee et al., *Genes Dev.* 7:555–69 (1993); Estojak et al., *Mol. Cell. Biol.* 15:5820–9 (1995). Contact between two proteins in these systems defines a physical relationship that is frequently of biological significance.

SUMMARY OF THE INVENTION

In general, the invention features a method for detecting a protein—protein interaction, involving: (a) providing a host cell which contains (i) a first reporter gene operably linked to a DNA sequence that includes a first protein binding site; (ii) a second reporter gene operably linked to a DNA sequence that includes a second protein binding site; (iii) a first fusion gene which expresses a first fusion protein, the first fusion protein including a first protein covalently bonded to a binding moiety which is capable of specifically binding to the first protein binding site; (iv) a second fusion gene which expresses a second fusion protein, the second fusion protein including a second protein covalently bonded to a binding moiety which is capable of specifically binding to the second protein binding site; and (v) a third fusion gene which expresses a third fusion protein, the third fusion protein including a third protein covalently bonded to a gene activating moiety; (b) measuring expression output of the first reporter gene as a measure of the interaction between the first and the third proteins; (c) measuring expression output of the second reporter gene as a measure of the interaction between the second and the third proteins; and (d) interpreting the expression output results of step (b) and step (c), whereby (i) increased output of both of the first and the second reporter genes indicates that the third fusion protein interacts with both of the first and the second fusion proteins; (ii) increased output of the first reporter gene but not the second reporter gene indicates that the third fusion protein interacts with the first fusion protein but not the second fusion protein; (iii) increased output of the second reporter gene but not the first reporter gene indicates that the third fusion protein interacts with the second fusion protein but not the first fusion protein; and (iv) no change in output in either of the first or the second reporter genes indicates that the third fusion protein does not interact with either of the first or the second fusion genes.

In a preferred embodiment, the method further involves comparing the expression output results of step (b) and step (c) with the expression output result measured in either (a) a first comparison host cell which contains (i) a reporter gene operably linked to a DNA sequence including a protein binding site; (ii) a first fusion gene which expresses a first fusion protein, the first fusion protein including the first protein covalently bonded to a binding moiety which is capable of specifically binding to the protein binding site; and (iii) a second fusion gene which expresses a second fusion protein, the second fusion protein including the third protein covalently bonded to a gene activating moiety; or (b) a second comparison host cell which contains (i) a reporter gene operably linked to a DNA sequence including a protein binding site; (ii) a first fusion gene which expresses a first fusion protein, the first fusion protein including the second protein covalently bonded to a binding moiety which is capable of specifically binding to the protein binding site; and (iii) a second fusion gene which expresses a second fusion protein, the second fusion protein including the third protein covalently bonded to a gene activating moiety; or (c) both of the first and the second comparison host cells. In addition, any number of comparisons may be made between multiple "two-bait" cells or between a "two-bait" cell and multiple "one-bait" cells, or both.

In other preferred embodiments, at least one of the first or the second reporter genes may be reduced in expression level; one of the first or the second protein binding sites is a tetracycline operator; one of the first or the second reporter genes is URA3 or lacZ; one of the first or the second reporter genes produces a signal that is received and detected by a second cell; the host cell is a yeast cell or a mammalian cell; the first and the second reporter genes may be expressed simultaneously; and the first protein and the second proteins are allelic variants.

In a second aspect, the invention features a method for detecting a protein that mediates a change in the state of another protein, involving: (a) providing a host cell which contains (i) a reporter gene operably linked to a DNA sequence including a protein binding site; (ii) a first fusion gene which expresses a first fusion protein, the first fusion protein including a first protein covalently bonded to a binding moiety which is capable of specifically binding to the protein binding site; and (iii) a second fusion gene which expresses a second fusion protein, the second fusion protein including a second protein which is capable of interacting with the first protein and which is covalently bonded to a gene activating moiety, wherein at least one of the first or the second proteins may exhibit a change in state; (b) allowing the first and the second proteins to interact; (c) measuring expression of the reporter gene as a measure of the interaction between the first and the second proteins; (d) introducing into the cell a third gene expressing a third protein; (e) measuring expression of the reporter gene, a change in the reporter gene expression in the presence of the third protein being an indication that the third protein mediates a change in the state of the first or the second protein leading to an alteration in the ability of the first protein and the second protein to interact.

In a related aspect, the invention features an alternative method for detecting a protein that mediates a change in the state of another protein, involving: (a) providing a first host cell which contains (i) a reporter gene operably linked to a DNA sequence including a protein binding site; (ii) a first fusion gene which expresses a first fusion protein, the first fusion protein including a first protein covalently bonded to a binding moiety which is capable of specifically binding to the first protein binding site; and (iii) a second fusion gene which expresses a second fusion protein, the second fusion protein including a second protein which is capable of interacting with the first protein and which is covalently bonded to a gene activating moiety, wherein at least one of the first or the second proteins may exhibit changes in state; (b) allowing the first and the second proteins to interact; (c) measuring expression of the reporter gene in the first host cell as a measure of the interaction between the first and the second proteins; (d) providing a second host cell which contains (i) the reporter gene operably linked to the DNA sequence including the protein binding site; (ii) the first fusion gene which expresses the first fusion protein; and (iii) the second fusion gene which expresses the second fusion protein; (iv) a third gene which expresses a third protein; (e) allowing the first and the second proteins to interact in the presence of the third protein; (f) measuring expression of the reporter gene in the second host cell as a measure of the interaction between the first and the second proteins in the presence of the third protein, a change in the reporter gene expression in the second host cell as compared to that measured in the first host cell being an indication that the third protein mediates a change in the state of the first or the second protein resulting in an alteration in the ability of the first protein and the second protein to interact.

In preferred embodiments of each of the above methods, the change in state is a conformational change; the protein exhibiting a conformational change is a Ras protein; the host cell is a yeast cell or a mammalian cell; the expression of the first fusion protein and the third protein occurs in response to an extracellular stimulus; and the reporter gene produces a signal that is received and detected by a second cell;.

In another related aspect, the invention features a cell that includes (i) a first reporter gene operably linked to a DNA sequence including a first protein binding site; (ii) a second reporter gene operably linked to a DNA sequence including a second protein binding site; (iii) a first fusion gene which expresses a first fusion protein, the first fusion protein including a first protein covalently bonded to a binding moiety which is capable of specifically binding to the first protein binding site; (iv) a second fusion gene which expresses a second fusion protein, the second fusion protein including a second protein covalently bonded to a binding moiety which is capable of specifically binding to the second protein binding site; and (v) a third fusion gene which expresses a third fusion protein, the third fusion protein including a third protein covalently bonded to a gene activating moiety.

In preferred embodiments, at least one of the first or the second reporter genes may be reduced in expression level; one of the first or the second protein binding sites is a tetracycline operator; one of the first or the second reporter genes is URA3 or lacZ; one of the first or the second reporter genes produces a signal that is received and detected by a second cell; and the host cell is a yeast cell or a mammalian cell.

In yet another related aspect, the invention features a reporter gene that includes a tetracycline operator operably linked to a gene encoding a detectable product (for example, a URA3 gene or a lacZ gene).

In a final aspect, the invention features a method for detecting whether a candidate protein interacts with a transcriptional activator, involving: (a) providing a host cell which contains (i) a reporter gene which can be reduced in expression level, the reporter gene being operably linked to a DNA sequence including a protein binding site; (iii) a first fusion gene which expresses a first fusion protein, the first fusion protein including the transcriptional activator covalently bonded to a binding moiety which is capable of specifically binding to the protein binding site; and (v) a second fusion gene which expresses a second fusion protein, the second fusion protein including the candidate protein covalently bonded to a gene activating moiety; (b) detecting an increase in expression of the reporter gene as an indication of an interaction between the candidate protein and the transcriptional activator.

In preferred embodiments, the reporter gene is a URA3 gene; the expression level is reduced by 6-azauracil; the protein binding site is a tetracycline operator; the expression level is reduced by tetracycline or a tetracycline derivative; and the host cell is a yeast cell or a mammalian cell.

By a "reporter gene" is meant a nucleic acid sequence whose expression may be assayed; such genes include, without limitation, lacZ, amino acid biosynthetic genes, and the mammalian chloramphenicol transacetylase (CAT) gene. Reporter genes may be assayed, for example, by a change in cell viability or color reaction.

By "expression output" is meant any measurable change in reporter gene expression.

By a "protein binding site" is meant a nucleic acid sequence that may be recognized and bound by a protein or peptide.

By a "transcriptional activator" is meant an amino acid sequence that is capable of increasing expression of a gene to which it is bound. A "gene activating moiety" is all or a portion of such a transcriptional activator that is capable of increasing gene expression.

By a "tetracycline derivative" is meant a compound that is related to tetracycline and that is capable of inhibiting the binding of a tetracycline repressor to a tetracycline operator. An exemplary tetracycline derivative is anhydrotetracycline.

By "a change in state" is meant any physical or chemical change in a protein that alters its activity. Examples of changes in state include changes in phosphorylation patterns or conformation.

Other features and advantages of the invention will be apparent from the following detailed description, and from the claims.

DETAILED DESCRIPTION

The drawings will first be described.

DESCRIPTION OF THE DRAWINGS

FIG. 2 is a table of results showing cells that register the logical "And" and discrimination relationships ("Ls1" and "Ls2") on interaction relationships $A_1$, and $A_2$. Cells contain the indicated bait and prey proteins; preys are only expressed on galactose and raffinose medium. Reporter output is indicated by growth or blue color on the indicated medium. For the And relationship, the prey protein contacts both baits and activates both reporters (TetOp-URA3 and LexOp-LacZ). For the Ls1 relationship, the prey interacts only with the LexA fusion bait, and activates only the LexOp-lacZ reporter. Similarly, in the Ls2 relationship, the prey contacts only the TetR fusion bait, and activates only the TetOp-URA3 reporter.

FIGS. 3A–3C are a series of results showing cells that register the logical And operation on input proteins. FIG. 3A is a table showing expression of the LexOp-LacZ reporter in CWXY2 cells 1 and 2; expression is indicated by the intensity of the blue color on LHWK/Gal+Raff+Xgal plates (see below) and by their β-galactosidase activity (indicated in Miller units). FIG. 3B is a schematic illustration of two cells with either TetR-Cdc25 (907–1589) or TetR-GAP, on Gal+Raff+Xgal medium (see below). In Cell 1 on the Gal+Raff plate, the TetR-Cdc25 loads LexA-RasA$_{186}$ with GTP, allowing binding of more B42-c-Raf1 and increased transcription of the LexAOp-lacZ reporter. In Cell 2, TetR-GAP stimulates Ras GTPase activity so that more LexA-Ras is in the GDP-form, resulting in less B42-c-Raf1 binding, and decreased transcription of the LexAOp-LacZ reporter. FIG. 3C is a truth table depicting the results of operations on protein inputs. In this figure, "1" in the second column denotes respectively the presence of TetR-Gap or TetR-Cdc25, and "0" or "1" in the third column denotes respectively a low or a high output of β-galactosidase.

Figure 1:
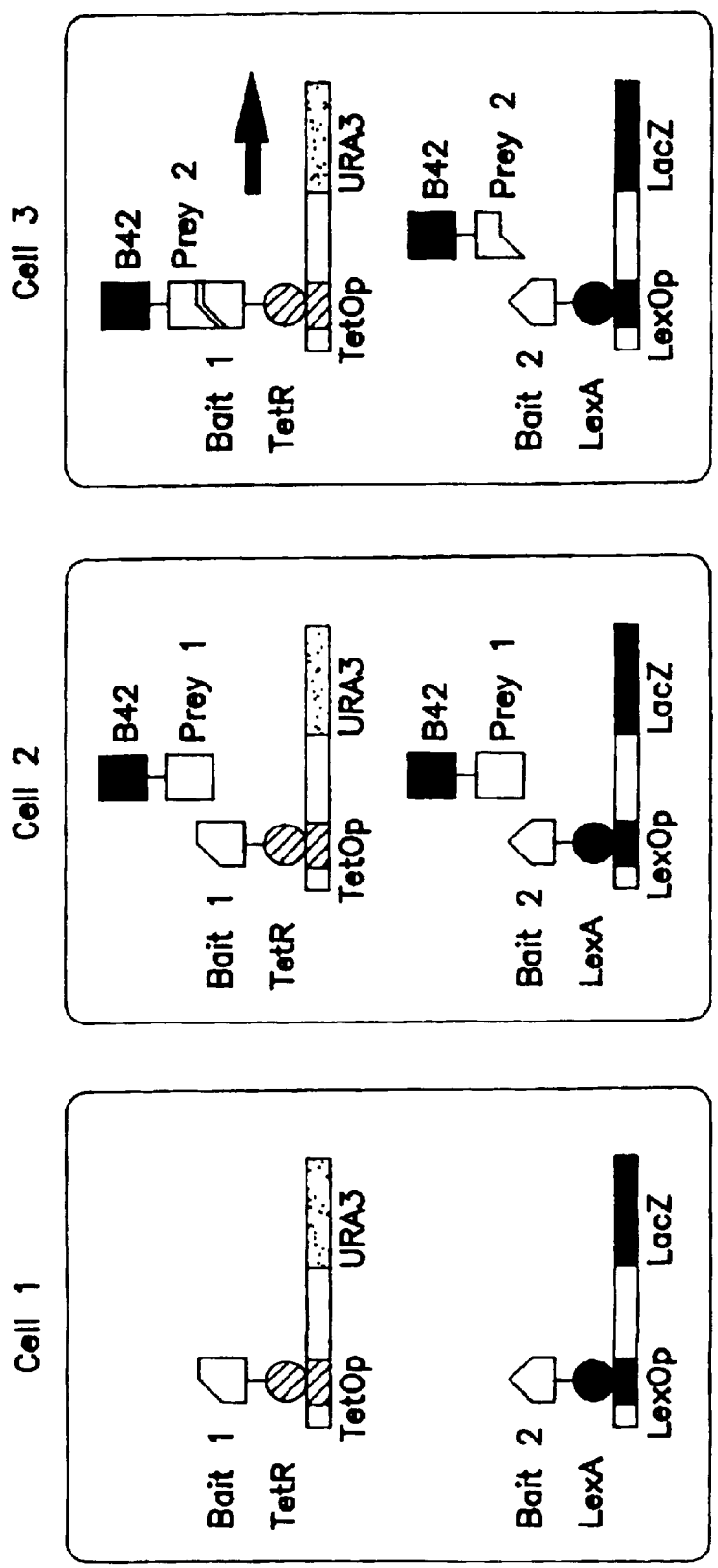
FIGS. 1A–1C is a series of three panels which schematically illustrate an exemplary two-bait interaction trap of the invention. In Cell 1 (FIG. 1A), on glucose medium, a transcriptionally-inert tetracycline repressor (TetR) fusion (Bait1, $Ba_1$) and a LexA fusion (Bait2, $Ba_2$) are bound to respective Tet and LexA operators upstream of reporters. The potentially interacting protein, fused to the transcription activation domain B42 is not expressed (Gyuris et al., *Cell* 75:791–803 (1993)). In this system, neither reporter gene is activated, the cell grows on 5-fluoroorotic acid (5-FOA) medium and does not grow on uracil⁻ medium, and is white on 5-bromo-4-chloro-3-indolyl-β-D-galactoside (Xgal) medium. In Cell 2 (FIG. 1B), on galactose and raffinose medium, Prey 1, a protein fused to B42, is expressed, but does not interact with either bait. The reporters are not activated, the cell grows on 5-FOA or does not grow on uracil⁻ medium, and is white on Xgal. In Cell 3 (FIG. 1C), on galactose and raffinose medium, another prey, Prey 2, is expressed and interacts with $Ba_1$, but not $Ba_2$. In this cell, the URA3 reporter is selectively expressed, the cell grows on uracil⁻ medium but is white on Xgal.

As described herein, the present invention provides methods and reagents for detecting or registering complex relationships between two or more proteins. Many of these relationships, for example, "bridging" (or connecting) and "discriminating" interactions, are useful for understanding gene function. As demonstrated below, by performing logical operations on the phenotypic outputs of both new and existing two-hybrid cell interactions, detailed models of protein function in pathways and complexes can be determined. The protein relationships detected by these cells are analogous to classical genetic relationships such as epistasis, but they can be interpreted within a rigorous analytical framework, and they can be performed systematically on the products of entire genomes. In addition, cells that register such relationships can perform logical operations on protein inputs, and thus may define paths for the construction of biological computational devices.

Preliminary Considerations: Logical Protein Relationships in Two-Hybrid Systems

In classical ("one bait") two-hybrid systems, the output of a reporter gene depends on the interaction between the DNA-bound bait and activation-tagged prey. Genetic markers expressed by some reporters, for example, URA3, allow selection against reporter transcription and thus for lack of interaction (Le Douarin et al., *Nucl. Acids Res.* 23:876–8 (1995)). The relationship between proteins in these systems can be described in symbolic-logical terms.

By this view, contact between a bait ($Ba_1$) and a prey ($P_1$) defines a variable ($A_1$), here called a contact relationship. Because $A_1$ is operationally defined by the reporter output, the term $A_1$ is used to refer to the reporter output as well. There are four possible Boolean operations, or functions, on this relationship (Schneeweiss, *Boolean Functions: With Engineering Applications and Computer Programs* (Springer-Verlag, Berlin, New York, 1989)). Two of these are constant functions: F1 ($A_1$)=0 and F2 ($A_1$)=1, and two are true functions: F3 ($A_1$)=$A_1$ and F4 ($A_1$)=Not A.

In one-bait systems, the phenotypic consequences of the reporter output can register two of these operations on the contact relationship, F3 and F4. This is shown in Table 1. In this Table, the contact relationship between the Bait $Ba_1$ and the Prey $P_1$ is denoted as $A_1$ and is measured by the output of the reporter. Thus, the values of $A_1$ (0 and 1) refer to both the values of the contact relationship and to the off and on states of the reporter. "Value of $A_1$" shows the two possible values (0 and 1 or off and on) of $A_1$. "Operation" shows the two allowed operations (functions) on $A_1$. The two subcolumns of "Results of operation" refer to the output of the operations on $A_1$. "Alternative names" gives common names for the operations. "Interpretation" describes the state of interaction between the bait and prey proteins. "Defining phenotype" gives the phenotype for a contact relationship in the one bait system, and "Example biological correlates" gives examples of the biological circumstances that can result in such outputs.

In Table 1, both F3 and F4 have important biological correlates. Consider a one bait system, in which contact between $Ba_1$ and $P_1$ (for example, because these proteins heterodimerize) gives a positive output (blue color on X-Gal, growth on Ura⁻ medium), while loss of that contact (for example, by mutation or disruption by a peptide aptamer) (Colas et al., *Nature* 380:548–550 (1996)) gives a negative output (white color on X-Gal, growth on 5-FOA medium) (Table 1). A cell growing on 5-FOA medium is analogous to a device that performs the logical Not operation on the contact relationship, or, alternatively, as a cell that registers the state (Not $A_1$).

Cells that Detect More Complex Protein Relationships

Cells were constructed that allowed simultaneous selection for and against two distinct protein—protein interactions (FIGS. 1A–1C). This two-bait interaction trap utilized the DNA binding moieties of LexA and TetR, the tetracycline repressor of bacterial transposon Tn10 (Gossen and Bujard, *Proc. Natl. Acad. Sci.* 89:5547–51 (1992)). The LexA and TetR fusion bait proteins were expressed in a yeast cell that also contained an integrated TetOp-URA3 reporter and an episomal LexAOp-lacZ reporter. Expression of baits in these "two-bait" cells was under the control of the ADH1 promoter. The TetOp-URA3 reporter was integrated into the LYS2 gene. The LexAOp-lacZ reporter, a derivative of pSH18–34, was carried on pCXW24, a 2 μm plasmid with a LYS2 marker. The prey vector was pJG4–5, whose GAL1 promoter conditionally directed expression of an activation-tagged protein from a 2 μm TRP1 plasmid (Gyuris et al., *Cell* 75:791–803 (1993)).

Logical Operations on a Contact Relationship in a Two-Bait Interaction Trap

In the two-bait cells, the two contact relationships (and the output of the corresponding reporters) were expressed as Boolean variables, $A_1$ and $A_2$. There were 16 possible operations on these variables (Schneeweiss, *Boolean Functions: With Engineering Applications and Computer Programs* (Springer-Verlag, Berlin, New York, 1989)), four of which were registered in these cells. These operations were referred to as And, Nor, and the two discrimination operations, logic state 1 (Ls1) and logic state 2 (Ls2). And, Ls1, and Ls2 were considered to represent particularly useful operations for determining protein function. A summary of these operations is shown in Table 2. In that Table, the contact relationship between $Ba_1$ and $P_1$ is denoted as $A_1$, and is measured by the output of the TetOp-URA3 reporter. The contact relationship between $Ba_2$ and $P_1$ is denoted as $A_2$, and is measured by the output of the LexAop-lacZ reporter. Again, values $A_1$ and $A_2$ (0 and 1) are used to refer to both the values of the contact relationship and to the values (off and on states) of the reporter. The four subcolumns of "Value of variables" denote the four different possible combinations of values for the two variables. "Operation" shows the four operations on these variables possible in this system. "Alternative names" gives common names for the operations. "Interpretation" describes the state of interactions between the bait and prey proteins. "Defining phenotype" gives the phenotype for touching relationship in the one bait system, and "Example biological correlates" gives examples of the biological circumstances that can result in such outputs.

To test the general utility of the system, a set of illustrative proteins were used, called $RasA_{186}$, $RasA15A_{186}$, $RasV_{12}A_{186}$, GAP, hSos1(residues 601–1019), Cdc25 (residues 907–1589), c-Raf1 (residues 1–313), Max, and Mxi1. The Harvey ras gene product, Ras, is a GTPase that exists in two distinct conformations, a GDP-bound (inactive) form and a GTP-bound (active) form. The fact that Ras cycles between these conformations allows it to be a switch protein in signal transduction pathways that control cell proliferation (Boguski and McCormack, *Nature* 366:643–654 (1993)). All Ras proteins described herein contained a Cys to Ala change at 186, which inactivated a farnesylation site and increased the apparent nuclear concentration of the protein. $RasA_{186}$ exists in a mixture of GDP and GTP bound forms, while $RasA_{15}A_{186}$ and $RasV_{12}A_{186}$ are predominantly in the GDP and GTP bound forms, respectively. GAP, which stimulates GTPase activity of Ras, binds to GTP-bound Ras. c-Raf1, a downstream target of Ras, also binds GTP-bound Ras. By contrast, hSos1 and Cdc25, both of which activate Ras, only bind to GDP-bound Ras. Max and Mxi1, which heterodimerize tightly, were used as positive controls (Zervos et al., *Cell* 79:388 (1993)).

FIG. 2 shows that the two-bait cell registered the logical And operation. The relationship is fulfilled by proteins, such as bridging proteins in pathways, that can interact with both baits. In this experiment, yeast strain CWXY2 carried B42-$RasA_{186}$ as prey, TetR-c-Raf1 and LexA-hSos 1 as the baits, and TetOp-URA3 and LexAOp-LacZ as the reporters. B42-$RasA_{186}$ interacted with both TetR-c-Raf1 and LexA-hSos1. The cell was blue on Xgal and grew on medium lacking uracil. This bridging or connecting relationship was consistent with the idea that Ras interacted with both proteins, and suggested that proteins that activate both reporters can be selected from genome-wide screens.

In addition, FIG. 2 shows that the two-bait system also registered Ls1 and Ls2, the discrimination relationships. These relationships are expected for proteins that interact with one bait but not another. Here, in cells expressing TetR-$RasV_{12}A_{186}$ and LexA-Max baits and a B42-c-Raf1 prey, the Ras-Raf interaction activated the TetOp-URA3 reporter, and the cells grew in medium lacking uracil; Raf did not interact with LexA-Max and thus did not activate the lacZ reporter. On the other hand, in a cell expressing TetR-$RasV_{12}A_{186}$ and LexA-Max baits and a B42-Mxi1 prey, the Max-Mxi1 interaction activated the LexAop-LacZ reporter, and the cells turned blue on Xgal; Mxi1 did not interact with Ras and thus did not activate the URA3 reporter.

Moreover, the results in FIG. 2 indicated that these cells could discriminate between two closely related allelic variants. In a cell expressing TetR-$RasA_{15}A_{186}$, LexA-$RasV_{12}A_{186}$, and B42-c-Raf1, the Raf/$RasV_{21}A_{186}$ interaction activated expression of the LexAop-LacZ reporter; the cells turned blue on Xgal but did not grow on medium lacking uracil. By contrast, in a cell expressing TetR-$RasA_{15}A_{186}$, LexA-$RasV_{12}A_{186}$, and B42-Cdc25, the Cdc25/$RasA_{15}A_{186}$ interaction activated the TetOp-URA3 reporter, and allowed the cells to grow on medium lacking uracil but caused it to remain white on Xgal. This result suggested that these cells could identify, from genomic or combinatorial libraries, proteins and peptides that interact with allelic protein variants specific for disease states.

Identification of Peptide Aptamers That Discriminate Between Allelic Variants

A two-bait cell that contained TetR-$RasV_{12}$ and LexA-$RasA_{15}$ was used to isolate members of a peptide aptamer library that interacted specifically with $RasV_{12}$. URA$^+$ library transformants were screened for lacZ$^-$ cells, which presumably contained aptamers that did not interact with LexA-$RasA_{15}$. Plasmids encoding aptamers were then rescued from these lacZ$^+$ cells and their phenotypes reconfirmed. Using this system, two discriminatory aptamers, Pep22 and Pep104, were identified. Pep22 interacted with both $RasV_{12}$ and $RasA_{15}$, whereas, by contrast, Pep104 interacted only with $RasV_{12}$. In particular, the Pep22-containing cell grew on Ura$^-$ medium and was blue on X-gal medium. The Pep104-containing cell grew on Ura$^-$ medium but was white on X-gal medium. These results demonstrated the utility of this system in selection of specific peptide aptamers. For Pep22, the second bait increased the selectivity of the system by eliminating potential false positives that might arise from artifactual activation of a single reporter. For Pep104, the second bait allowed detection of aptamers specific for an allelic form of the protein active in signal transduction. The sequences of Pep22 and Pep 104 are DMDWFFRFYA SVSRLFRHLH (SEQ ID NO:15) and FWQATLRLVS DKLILLYPDP (SEQ ID NO:16), respectively.

Logical Operations on Protein Inputs

Cells can also perform logical operations on protein inputs, and register the result of those operations by changes in output. FIGS. 3A–3C show a logical And operation on protein inputs. In a cell expressing LexA-RasA$_{186}$, B42-c-Raf1, and TetR-GAP, the output of the LexAop-lacZ reporter was low (light blue on Xgal medium), presumably because GAP drove most of the Ras to the GDP-bound conformational state. By contrast, input of TetR-Cdc25 increased the RasA$_{186}$/c-Raf1 interaction, as shown by the intensity of blue color on Xgal plates, presumably by changing Ras into the Raf binding conformation. In this experiment, the cell had two inputs, one of which, B42-c-Raf1 (logical value 1) was constantly present, while the other was either TetR-GAP (logical value 0) or TetR-Cdc25 (logical value 1); and the output was either high (1) or low (0). In this case, the output of the LexAop-lacZ reporter was thus controlled by a LexA-Ras switch protein whose conformation depended on the values of the inputs.

In an alternative to the above system, Cdc25 may be replaced with hSos1, and similar results obtained. In addition, expression of system components may be further regulated. For example, in the systems described above, B42-c-Raf1 may be expressed using a GAL1 promoter, and/or Cdc25 and hSos1 may be expressed from a promoter normally repressed by TetR-Sin3. This results in expression of B42-c-Raf1 being dependent on the presence of galactose in the growth medium, and expression of Cdc25 and hSos1 being dependent on the presence of tetracycline or a tetracycline derivative in the growth medium. In these systems, the cell is responding to two distinct extracellular inputs, one that controls the expression of the modifying protein and the other that controls expression of the prey.

Protein Relationships in Two Hybrid Systems

Based on the experiments described above, the outputs of reporter genes in one bait two-hybrid systems may be viewed as reflecting two basic logical states. The activation of the reporter gene embodies the contact relationship Al between the bait 1 (Ba$_1$) and prey (P$_1$). Not A$_1$ (between Ba$_1$ and P$_1$) defines the lack of interaction, caused, for example, by a mutation in the interacting partners, or disruption of the interaction by a third protein or peptide aptamer (Colas et al., *Nature* 380:548–550 (1996)).

Construction of Cells with Independently Functional Interaction Reporters

As described above, cells were constructed that detected more complex protein relationships by making a version of the interaction trap that utilized the DNA binding moieties of LexA and TetR, the tetracycline repressor of bacterial transposon Tn10. Fusion proteins containing these moieties were expressed as two baits in a cell that also contained TetOp-URA3 and LexAop-lacZ reporters. This system allowed simultaneous determination of two genetic interactions in a single cell.

The inclusion of TetR baits and TetOp-URA3 reporters significantly facilitated interaction trap applications. The phenotype dependent on the TetOp-URA3 reporter was more sensitive than that of lacZ and LEU2 reporters (see, for example, Gyuris et al., *Cell* 75:791–803 (1993) and Estojak et al., *Mol. Cell. Biol.* 15:5820–9 (1995)) which facilitates detection of weak interactions. In addition, both the URA3 and LacZ reporter genes may be quantitatively assayed (Shostak et al., *Anal. Biochem.* 191:365–9 (1990)). Moreover, the sensitivity of this URA3 reporter can be down-regulated in two ways. Expression of the URA3 reporter can be titrated by 6-azauracil, an inhibitor of the URA3 gene product (orotidine-5'-monophosphate decarboxylase (OMPdecase) (Le Douarin et al., *Nuc. Acids Res.* 23:876–8 (1995)). Reporter activity can also be reduced by tetracycline or its derivatives (for example anhydrotetracycline), which disrupt binding of the TetR bait to Tet operators. Preferably, such compounds are used at a concentration of up to 100 μg/ml on plates. Both kinds of inhibitors diminish the sensitivity of the URA3 reporter, allowing its use with baits that activate transcription and allowing its use, along with lacZ, for crude estimation of interaction affinities. Moreover, the URA3 reporter allows the use of 5-FOA to select against gene expression (Boeke et al., *Mol. Gen.Genet.* 197:345–6 (1984)). In this case, tetracycline and 6-azauracil can regulate the threshold amount of transcription selected against, facilitating the selection of peptide aptamers that break specific protein interactions.

Logical Analysis of Binary and Higher-Order Protein Relationships

As shown in Table 2, the two bait cells registered four logical relationships, Nor, And, Ls1, and Ls2. Three are particularly important. The And relationship (A$_1$ (between Ba$_1$ and P$_1$) and A$_2$ (between Ba$_2$ and P$_1$) was found for prey proteins (connecting proteins) that contacted both baits (Table 2). Identification of such proteins is useful for continued construction of dense charts of genetic networks and for connecting pathways not previously known to be related. Such sets of interacting proteins are sometimes referred to as "protein contigs."

Ls1 and Ls2, the discrimination relationships, were also important. These relationships are relatively complex: for example, the Ls1 relationship involves two operations on two interactions: Not A$_1$ (between Ba$_1$ and P$_1$) and A$_2$ (between Ba$_2$ and P$_1$). These operations have numerous biological correlates, in that a cell that registers this relation allows detection of proteins that interact differently with unrelated proteins, allelic variants, and different conformational states (FIG. 2), and also allows detection of proteins that interact differentially with different modification states. The use of these relationships to survey the products of combinatorial libraries and genomes allow selection of proteins that interact specifically with proteins encoded by disease-state alleles, or with proteins that differ from wild-type due to differential splicing or posttranslational modification.

Analysis of Higher-Order Protein Relationships

The protein relationships that can be inferred from two-bait cells are not always identical to those revealed by one-bait cells. For example, if both Ba$_1$ and Ba$_2$ oligomerize to form a surface that interacts with P, then neither the Ba$_1$/P nor Ba$_2$/P interaction will be detected in one-bait cells. Such differences in contact relationships are useful, since combining data from one- and two-bait cells allows the experimenter to make inferences about the topology, temporal sequence, and posttranslational modification dependent of the protein interactions.

Table 3 shows inferences about physical interactions among three proteins, X, Y, and Z: (i) from possible outputs of a two-bait cell that detects contact relationships $A_1$ (between X and Z), $A_2$ (between Y and Z), and $A_3$ (between X and Y). In this Table, "reporter output" shows the state of the contact relationships registered by outputs of the reporters in three one-bait cells and a single two-bait cell. X and Z are fused to an activation domain to form preys [P(X) and P(Z)], and Y and X are fused to a DNA binding domain to form baits [Ba(X) and Ba(Y)]. In a two-bait cell, the outputs of the reporters show the state of the contact relationship for proteins X, Y, and Z where they are fused with one of two DNA binding domains [$Ba_1$(X) or $Ba_2$(Y)] and an activation domain [P(Z)]. "Physical interpretation" shows one possible biological interpretation of this set of reporter outputs for combinations of one- and two-bait data, or for one-bait data alone. Although all patterns in Table 3 may not have biological correlates, many have been observed, for example, the interaction of $Bait_1$ and prey depends on the presence of $Bait_2$. Experiments such as those depicted in Table 3 indicating linkages of one- and two-bait data are useful in ordering the function of proteins in pathways and complexes.

Application to the Analysis of Gene Function

This two-bait system, particularly when combined with existing one bait systems, thus extends the scope of yeast interaction technology to analyze the function of genes in pathways. It can aid the identification of proteins and peptide aptamers that distinguish between allelic variants of proteins. In addition, linkage of data from two-bait cells (likely to result from individual experiments) and from one-bait cells (perhaps obtained from genome-wide surveys) allows detailed analysis of protein function and contact topology in pathways and complexes. It also allows more precise analysis of the topology of proteins in multi-protein complexes, and it provides robust, scalable, semi-automatic ways to distinguish among alternative models of protein interactions. In addition, because the relationships among proteins defined in this way lend themselves to systematic analysis, they can be determined industrially.

Towards Protein-and-Transcription Based Logical Circuitry

The above experiments made use of a protein, Ras, that cycles between two conformational states, and an activation tagged protein, Raf, that binds Ras in one of these states. The state of the Ras switch, and its output measured by transcription, was shown to vary, depending on whether the input protein was GAP or Cdc25. In these experiments the cells were acting as And gates, in which one input, B42-c-Raf1, was held constant (logical value 1), the other was either Gap (logical value 0) or Cdc25 (logical value 1), and the phenotypes caused by expression of the reporters constituted the outputs. With B42-c-Raf1 and GAP, the output was low β-galactosidase activity (0). With B42-c-Raf1 and Cdc25, the output was high β-galactosidase activity (1). Although it was also scored by reporter expression, this And operation was not an operation on the contact relationship like those described earlier. Rather, the operation was on the protein inputs, and in this case the cells were acting as true logic gates.

In the cells described herein, to change the inputs, different DNA constructions were employed that expressed interacting proteins; to measure output, human or other observers were needed. Construction of wholly biological transcription-based logic circuitry requires replacing these inputs and outputs with logical inputs that vary in response to extracellular stimuli, such as secreted peptide pheromones or light, and outputs that generate such stimuli.

Figure 4:
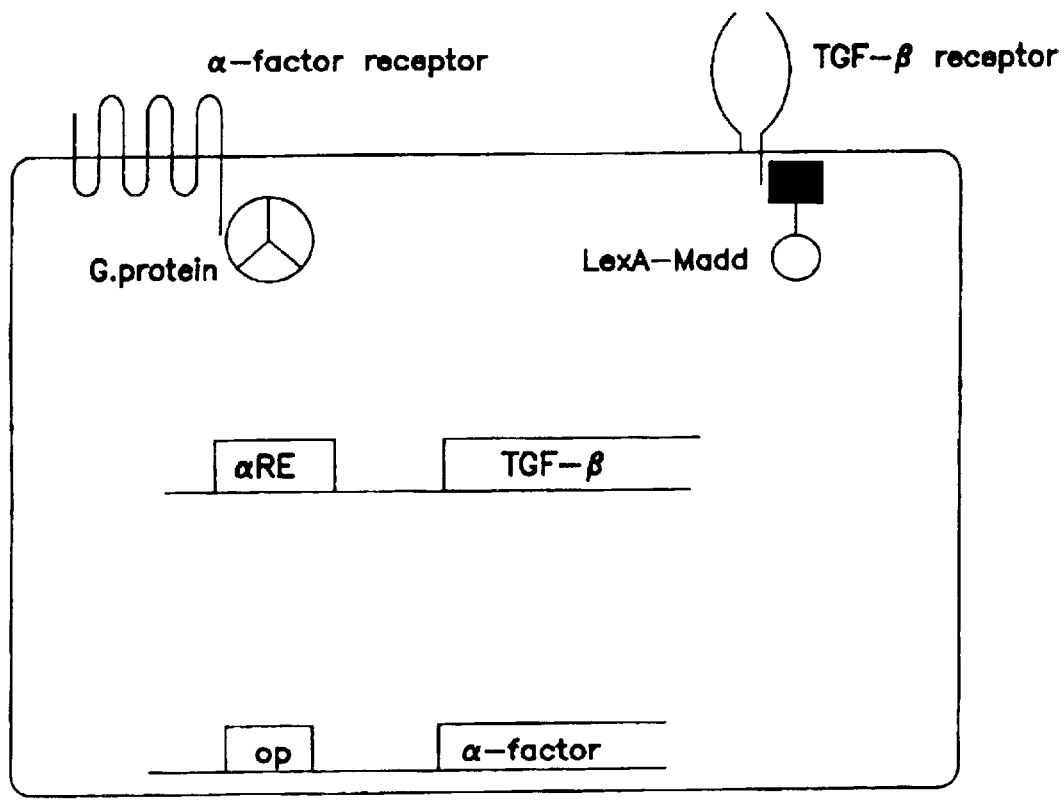
FIG. 4 is a schematic illustration of a cell that produces an output that may be read by the producer cell or a second, recipient cell.
Figure 5:
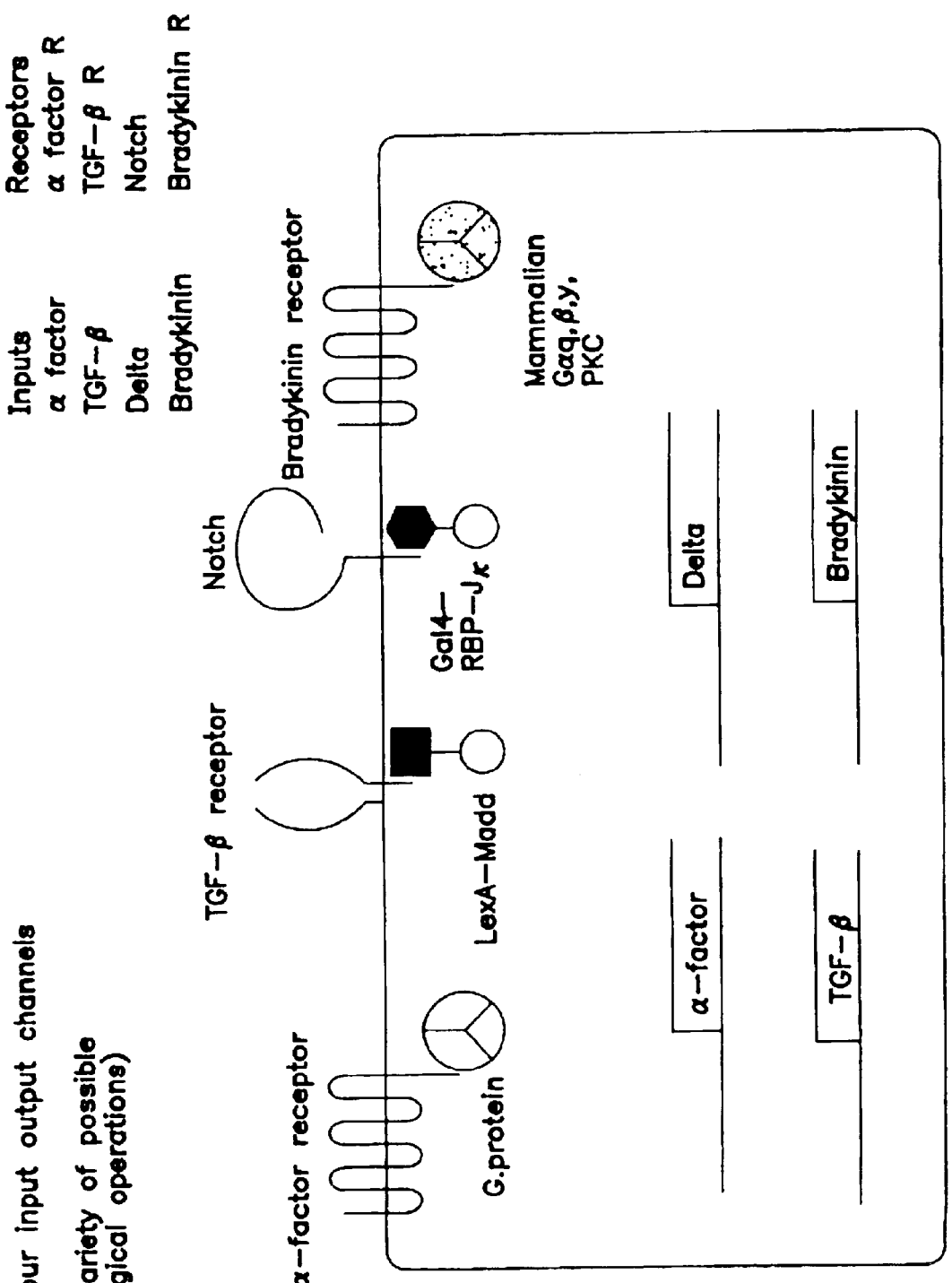
FIG. 5 is a schematic illustration of a cell having four input-output channels.
Figure 6:
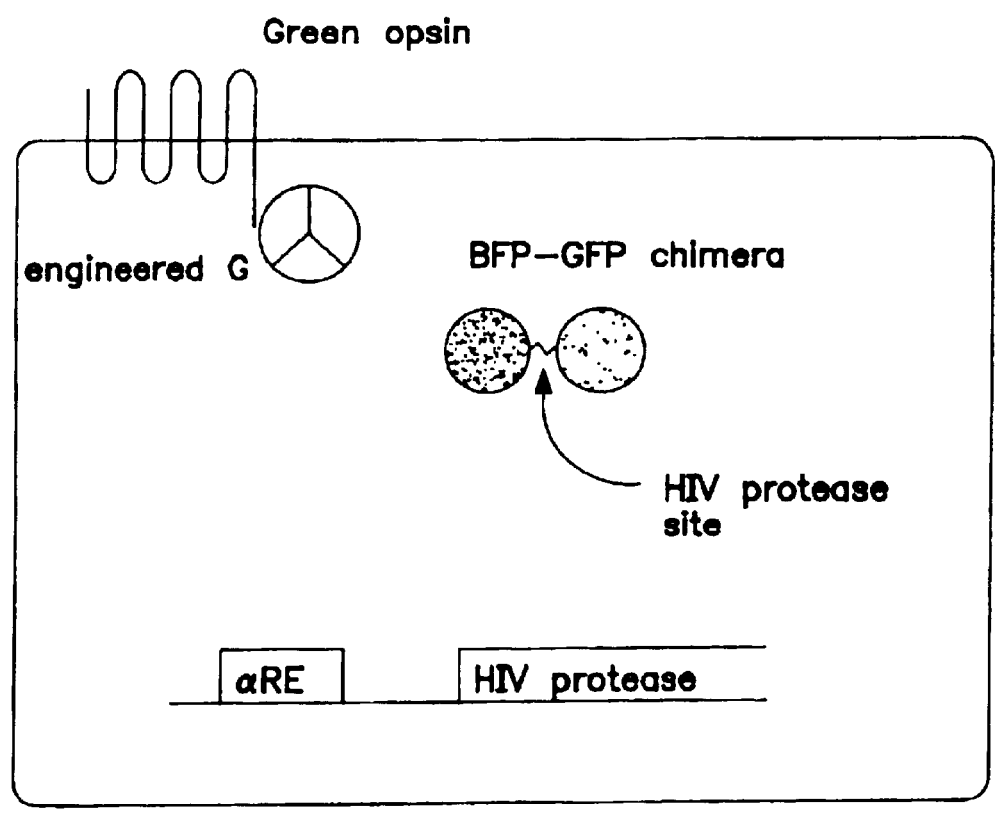
FIG. 6 is a schematic illustration of a wholly biological circuit that acts as a transistor.

Exemplary systems employing such biological circuitry are shown in FIGS. 4–6. In particular, in FIG. 4, a cell is depicted that produces an output that may be read by the producer cell or by a second, recipient cell in response to the input. As shown in FIG. 4, addition of the input protein, yeast α-factor, results in the expression, through a G protein pathway, of a TGF-β output, an output that may be received by the same or a second cell and that may produce a phenotypic change in the recipient cell. FIG. 4 also depicts a system in which a TGF-β input protein binds to its receptor, resulting in the activation and translocation of a LexA-Madd (also referred to as a LexA-Smad) protein. This LexA-Madd protein triggers expression of a yeast α-factor output, a signal that again may be read by the producer cell or by a second, recipient cell and may produce a phenotypic change in the recipient cell.

FIG. 5 extends this system and illustrates a cell having four different input-output channels, thereby allowing for a variety of logical operations. In FIG. 5, the input proteins α-factor, TGF-β, delta, and bradykinin interact with the α-factor receptor, TGF-β receptor, notch receptor, and bradykinin receptor, respectfully, to activate pathways that result in expression of output proteins that may be read by cellular systems, for example, as transcriptional changes. As the number of input and output options increases, the number of channels that may be programmed increases; for example, a cell having 10 input/output channels may be programmed in $2^{10}$, or more than 1000 different states. In one exemplary approach to increasing input/output channels, a protein, such as the LexA-Smad protein discussed above, may be engineered to contain different aptameric moieties, each conferring a different receptor specificity on the chimera. Moreover, in these systems, the input, rather than being a protein, may be some other extracellular stimuli, such as light or a particular wavelength of light that triggers a specific photoreceptor pathway. Preferably, in such a system, the output is a fluorescent protein, for example, a green, red, or blue fluorescent protein.

One final type of wholly biological circuit is depicted in FIG. 6. This cell represents an exemplary "transistor." In this cell, in the presence of green light, a reporter gene is triggered to express an HIV protease. This protease then cleaves a target linker that joins together a blue fluorescent protein-green fluorescent protein chimera, releasing both components, and resulting in a large decrease in green light output.

The wholly biological logical devices described above might not be very fast. Although one of these switch proteins, Ras, can cycle in milliseconds and a number of signal transduction pathways can provide inputs within minutes (Bray, Nature 376:307–312 (1995)), reporter output may require minutes to hours to be detectable. However, because required construction work near the DNA may be performed using straightforward techniques, it is likely that gene expression will remain a useful output. Construction of such circuits is facilitated by the rapid increase in the number of natural and artificially selected protein domains with useful allosteric and targeting properties (Colas et al., Nature 380:548–550 (1996)). It is thus possible that such transcription-based technologies provide an early route to biological computation.

Material and Methods

The Two-Bait System

In the experiments described above, the vectors pEG202 and pJG4–5 were utilized as $Ba_2$ and prey expression plasmids (Gyuris et al., Cell 75:791–803 (1993)). In addition, Ba₁ expression plasmid, pCWX200, LexAOp-LacZ reporter plasmid, pCWX24, and TetOp-URA3 reporter vectors were constructed and were integrated into *Saccharomyces cerevisiae* strains to create CWXY1 and CWXY2 as follows.

Construction of the TetR-fusion protein expression vector, pCWX200. pCWX200 carried a 2 μm replicator and LEU2 marker. The promoter and cloning region derived from pEG202 and the backbone from pBC100, a derivative of Yeplac 181 (Gietz and Sugino, Gene 74:527–534 (1988)). To remove the pBC100 polylinker region (from AccI to EcoRI) as well as DNA encoding the amino-terminal fragment of β-galactosidase, the vector was digested with NarI/AccI and religated to yield pCWX100. The HindIII site was then deleted by digesting pCWX100 with HindIII, blunt-ending the overhangs with Klenow, and religating to yield pCWX100ΔHindIII. The SphI fragment of pEG202, containing the ADH1 promoter, LexA, a polylinker, and the ADH1 terminator was then inserted into the SphI site of pCWX100ΔHindIII to yield pCWX150 (Gyuris et al., Cell 75:791–803 (1993) and Estojak et al., Mol. Cell. Biol. 15:5820–9 (1995)). Finally, the EcoRI/HindIII LexA fragment of pCWX150 was replaced with an EcoR1HindIII ended PCR fragment that encoded the Tet repressor (TetR) (Zervos et al., Cell 79:388 (1993)). The resulting plasmid, pCWX200, had cloning sites equivalent to those of pEG202 (Gossen and Bujard, Proc. Natl. Acad. Sci. 89:5547–51 (1992)).

Construction of the LexAop-lacZ reporter, pCWX24. The LexAop-lacZ reporter, the LYS2 marker, the 2 μm replicator, and the rest of the pCWX24 plasmid backbone were derived from intermediate plasmids pCWX221, pCWX01, and pCWX21, respectively.

Construction of pCWX221. To construct this plasmid, SH18–34T was digested to completion with KpnI, a partial digestion with BamH1 was performed, and the vector was ligated to a BamHI/KpnI digested backbone of pBluescript. The LexAOp-LacZ reporter was on the NotI/KpnI fragment of pCWX221.

Construction of pCWX01. To construct pCWX01, YeP426 was digested with SalI/ClaI (Ma et al., Gene 58:201–16 (1987)), and a ~5600 bp ClaI-XbaI fragment was obtained that carried LYS2 (Barnes and Thorner, Mol. Cell. Biol. 6:2828–38 (1986)) and about 300 bp of the pBR322 tetracycline resistance gene. This fragment was ligated with the (pBluescriptΔKpnI) pBSΔKpnI backbone digested with ClaI/SalI, to generate pCWX01.

Construction of pCWX21. pRF24 was digested with NotI and blunt-ended with Klenow to yield pCWX20ΔNotI. To create pCWX21, pCWX20ΔNotI was digested with BamHI and ligated to self-annealed 5'-GATCCGCGGCCGCG-3' (SEQ ID NO:1) to generate a new NotI site.

Assembly of pCWX24. To assemble pCWX24 aNotI/KpnI LexOp-LacZ fragment of pCWX221 was inserted into the NotI/KpnI site of pCWX21 to create pCWX22. Next, a self-annealed 5'-CTAGGGCCCTAGCATG-3' (SEQ ID NO: 17) fragment was inserted at the SphI site of pCWX22 to generate an ApaI site and the vector pCWX23. After digesting pCWX23 with ApaI/PmeI, a SmaI/ApaI digested LYS2 fragment of pCWX01 was inserted to create pCWX24.

Construction of TetOp-URA3. The TetOp-URA3 constructs were generated from the intermediate plasmids, pCWX211, pCWX213T2, pCWX213T10, pCWX02T2, and pCWX02T10.

Construction of pCWX211. Following amplification of the URA3 gene from pSH200 with 5'-AAAAGGAAAAGCGGCCGCTTAGTTTTGCTGGCCGCATCTTC3' (SEQ ID NO: 2) and

5'-CGGAATTCTTTCGAAAGCTACATATAAGGAAC-3' (SEQ ID NO: 3), the NotI/EcoRI ended PCR product was ligated to EcoRI/NotI-digested pBS to generate pCWX211.

Construction of pCWX213T2 and pCWX213T10. To construct these vectors, a BamHI fragment from pLR1Δ1, containing the yeast Gal1/Gal10 promoter region with a unique XhoI site (West et al., Mol. Cell Biol. 4:2467–78 (1984)), was inserted into the BamHI site of pBS to create pCWX210. Two strands were then synthesized and annealed to create an XhoI/SalI-ended DNA fragment that contained two TetO₂ operators (Meier et al., EMBO J. 7:567–72 (1988)), as follows (SEQ ID NOS:4 and 5):

```
                              *                              *
               _____-_____      _____-_____
               TCGAGcactccctatcagtgatagagaaaacactccctatcagtgatagagaaaaG
           1---------+---------+---------+--------+---------+------56
                              CgtgagggatagtcactatctcttttgtgagggatagtcactatctcttttCAGCT
```

After ligating the Tet operator DNA to itself, it was digested with XhoI/SalI and fractionated on a 0.8% agarose gel. DNA with sizes ranging from 100 bp to 200 bp was inserted at the XhoI site of pCWX210. Using this protocol, two plasmids, pCWX210T2 and pCWX210T10, were obtained, which contained 4 and 6 TetO₂ operators respectively. The EcoRI-ended Gal1/Gal10 promoter regions of pCWX210T2 and T10 were inserted into the EcoRI site of pCWX211 to generate pCWX211T2 and pCWX211T10 respectively. In addition, a KpnI site in these plasmids was created by inserting a self-annealed oligo (5'-GGCCGCGGTACCGC-3') (SEQ ID NO:6) at the NotI site to create pCWX212T2 and pCWX212T10 respectively. In these vectors, the TetOp-URA3 reporter was positioned on a KpnI fragment. Deletion of the ClaI site in these plasmids produced plasmids, pCWX213T2 and pCWX213T10. Replacement of the KpnI fragment of LYS2 from pCWX01 with KpnI-ended TetOp-URA3 constructs from pCWX213T2 and pCWXT10 created pCWX02T2 and pCWX02T10.

Integration of the TetOp-URA3 Reporter at LYS2. Following digestion of pCWX02T2 and pCWX02T10 with ClaI/XbaI, these vectors were transformed into *Saccharomyces cerevisiae* strain EGY40 containing pCWX200Cdi2 (Gietz et al., *Yeast* 11:355–60 (1995)), a vector which directed expression of the TetR-Cdi2 gene, a transcription activator (Finley and Brent, *Proc. Natl. Acad. Sci.* 91:12980–84 (1984)). Transformants were selected on medium lacking uracil and leucine. Ten independent clones were picked for each pCWX02T2 and pCWX02T10 transfomation, and streaked them onto alpha-aminoadipic acid plates to select for those in which LYS2 was inactivated (Chattoo et al., *Genetics* 93:51–65 (1979)). Integration of the TetOp-URA3 gene at the LYS2 locus was confirmed by PCR using primers which hybridized to the regions flanking the KpnI fragment of LYS2. The resulting strains CWXY1 and CWXY2 (MATa ura3 his3 trp1 leu2 lys2Δkpn::TetOp-URA3) contained 4 and 6 $TetO_2$ operators upstream of the URA3 gene, respectively.

Assays for the And and Discrimination Relationships

To assay interaction relationships, a series of vectors were constructed. c-Raf1 (1–313) was cloned into the EcoR1/Xho1 sites of vectors pCWX200 and JG4–5. Following amplification of $RasA_{15}A_{186}$, hSos1(601–1019), and Cdc25 (907–1589) with $RasA_{15}A_{186}$ primers

```
5'-GCCTGAATTCATGACGGAATATAAGCTGG3'      (SEQ ID NO: 7) and

5'-CCCGAACTCGAGTCAGGAGAGCACTGCCTTGCAGC-3' (SEQ ID NO: 8), the hSos1 (601-1019) primers 5'-GCCTGAATTCAAAGCAGGAACTGTT-3'          (SEQ ID NO: 9) and

5'-CCCGAACTCGAGCTATCGTGGTTCTATTTCTAG-3'  (SEQ ID NO: 10), and the Cdc25 catalytic domain (907-1589) primers 5'GCCTGAATTCATGTCTTCGGTCTCCTCAG-3'       (SEQ ID NO: 11) and

5'-CCCGAACTCGAGTTATCGAAATAACCTAGAAGG-3'  (SEQ ID NO: 12),
``` the EcoRI/XhoI-ended PCR products of $RasA_{15}A_{186}$, hSos1 (601–1019), and Cdc25(907–1589) were also cloned into the EcoR1/Xho1 sites of vectors pEG202 and pJG4–5. Having transformed CWXY2 containing pCWX24 with the combinations of two baits and preys as above in FIG. 2, transformants were streaked onto dropout plates lacking leucine, histidine, lysine, and tryptophan ("LHKW"), having glucose as a carbon source ("Glu"), and supplemented with 100 μg/ml 6-Azauracil, an inhibitor of URA3 (Le Douarin et al., *Nucl. Acids Res.* 23:876–8 (1995)). These plates were incubated at 30° C. for 12–48 hours. Yeast streaks were next replicated onto the four dropout plates, LHKW/Glu+X Gal, LHKW/Galactose (Gal)+Raffinose (Raff)+X Gal, LHKWU/Glu, and LHKWU/Gal+Raff as shown above, and the results were scored after incubation at 30° C. for 12–72 hours.

Assays for the And Operation on Protein Inputs

To carry out additional assays, an EcoRI/XhoI-ended PCR product of human GAP1, amplified with primers 5'-GCCTGAATTCATGAAGGGGTGGTATCACGGA-3' (SEQ ID NO:13) and 5'-CCCGAACTCGAGCTA-CTTGACATCATTGGTTTTTG-3' (SEQ ID NO:14), was cloned into pCWX200. EcoRI/XhoI-ended Cdc25(907.-1589) (as in FIG. 2) was also cloned into pCWX200. CWXY2 containing pEG202RasA$_{186}$ and pJGRaf(1–313) was then further transformed with either pCWX200, pCWX200CDC25(907–1589), or pCWX200GAP. Streaks of transformants pooled from >50 independent transformants were replicated onto LHKW/Glu+Xgal and LHKW/Gal+Raff+Xgal dropout plates, and these plates were incubated at 30° C. for 2–3 days. Cells on the former plate showed no blue color, and, on the latter plate, showed blue color of varied intensity. β-galactosidase activity was measured by liquid assays in triplicates of cell pools (Estojak et al., *Mol. Cell Biol.* 15:5820–9 (1995)), each of which contained >50 independent transformants. After inoculating LHKW/Gal+Raff medium at an $OD_{600}$ of 0.2 with washed cells grown to late log phase or saturation in LHKW/Glu liquid media, cultures were incubated at 30° C. for an additional 5 hours, and β-galactosidase assays were performed as described in Estojak et al. (Mol. Cell Biol. 15:5820–29 (1995)).

TABLE 1

| | | Alternative name | Interpretation | Defining phenotype | Example biological correlates |
|---|---|---|---|---|---|
| Variable | Value of A1 | | | | |
| $A_1$ | 0 1 | | | | |
| Operation | Results of operation | | | | |
| F3 | 0 1 | Identity | Interaction | Growth on URA⁻ | Proteins touch |
| F4 | 1 0 | Not | No interaction | Growth on 5-FOA | Interaction disrupted by mutation in one protein, competed by third protein or peptide aptamer |

TABLE 2

| Variable | Value of variable | Alternative name | Defining Phenotype | Interpretation |
|---|---|---|---|---|
| $A_1$ | 0 1 0 1 | | | |
| $A_2$ | 0 0 1 1 | | | |
| Operation | Result of operation | | | |
| F2 | 1 0 0 0 | Nor | White on X-Gal and no growth on URA⁻ or Growth on 5-FOA | No interaction of $Ba_1/P_1$ or $Ba_2/P_1$ |
| F9 | 0 0 0 1 | And, bridging, $A_1$ And $A_2$ | Blue on X-Gal and Growth on URA⁻ | $P_1$ interacts with $Ba_1$ and $Ba_2$ |
| F3 | 0 0 1 0 | Ls1, Discrimination, (Not $A_1$) And $A_2$ | White in X-Gal and Growth on URA⁻ | $P_1$ interacts with $Ba_2$ not $Ba_1$ |
| F5 | 0 1 0 0 | Ls2, Discrimination, $A_1$ And (Not $A_2$) | Blue on X-Gal and no growth on URA⁻ or growth on 5-FOA | $P_1$ interacts with $Ba_1$ not $Ba_2$ |

TABLE 3

| Reporter output | | | | | | |
|---|---|---|---|---|---|---|
| One bait cells | | | Two bait cells | | | |
| $A_1$ Ba(X) P(Z) | $A_2$ Ba(Y) P(Z) | $A_3$ Ba(X) P(Y) | $A_1$ $Ba_1$(X) P(Z) | $A_2$ $Ba_2$(Y) P(Z) | Physical interpretation (one-bait and two bait combined) | Physical interpretation (one-bait data only) |
| 0 | 0 | 0 | 0 | 0 | X, Y, Z do not interact | X, Y, Z, do not interact |
| 0 | 0 | 0 | 0 | 1 | X, Y, Z associate weakly, modified y and/or z interact | X, Y, Z do not interact |
| 0 | 0 | 0 | 1 | 0 | X, Y, Z associate weakly, modified X and/or Z interact | X, Y, Z do not interact |
| 0 | 0 | 0 | 1 | 1 | X, Y, Z form trimer, requires X, Y, and Z | X, Y, Z do not interact |
| 0 | 0 | 1 | 0 | 0 | X, Y form dimer | X, Y form dimer |
| 0 | 0 | 1 | 0 | 1 | X modifies Y, modified Y binds Z | X, Y form dimer |
| 0 | 0 | 1 | 1 | 0 | Y modifies X, modified X binds Z | X, Y form dimer |
| 0 | 0 | 1 | 1 | 1 | X, Y form dimer, Z binds X/Y dimer to form X/Y/Z trimer | X, Y form dimer |
| 0 | 1 | 0 | 0 | 0 | X breaks Y/Z dimer | Y, Z form dimer |
| 0 | 1 | 0 | 0 | 1 | Y, Z form dimer, Z discriminates between X and Y | Y, Z form dimer |
| 0 | 1 | 0 | 1 | 0 | Y modifies Z, modified Z binds X | Y, Z form dimer |
| 0 | 1 | 0 | 1 | 1 | Y, Z form dimer, X binds to Y/Z dimer to form X/Y/Z trimer | Y, Z form dimer |
| 1 | 0 | 0 | 0 | 0 | Y breaks X/Z dimer | X, Z form dimer |
| 1 | 0 | 0 | 0 | 1 | X modifies Z, modified Z binds Y | X, Z form dimer |
| 1 | 0 | 0 | 1 | 0 | X, Z form dimer, Z discriminates between X and Y | X, Z form dimer |
| 1 | 0 | 0 | 1 | 1 | X, Z form dimer, Y binds to X/Z dimer to form X/Y/Z trimer | X, Z form dimer |
| 0 | 1 | 1 | 0 | 0 | X, Y and Y, Z form dimers, X/Y dimer precludes Y binding Z | Y, Z and Y, X form dimers |
| 0 | 1 | 1 | 0 | 1 | X, Y and Y, Z form dimers, Y/Z dimer precludes X binding Y | Y, Z and Y, X forms dimers |
| 0 | 1 | 1 | 1 | 0 | Y modifies X, modified X binds Z | Y, Z and Y, X forms dimers |
| 0 | 1 | 1 | 1 | 1 | X/Y and Y/Z dimers interact through Y to form X/Y/Z trimer | Y, Z and Y, X form dimers |
| 1 | 0 | 1 | 0 | 0 | X, Y and X, Z form dimers, X/Y dimer precludes X binding Z | X, Z and X, Y form dimers |
| 1 | 0 | 1 | 0 | 1 | X modifies Y, modified Y binds Z | X, Z and X, Y form dimers |
| 1 | 0 | 1 | 1 | 0 | X, Y and X, Z form dimers, X/Z dimer precludes X binding Y | X, Z and X, Y form dimers |
| 1 | 0 | 1 | 1 | 1 | X/Z and X/Y dimers interact through X to form X/Y/Z trimer | X, Z and X, Y form dimer |
| 1 | 1 | 0 | 0 | 0 | X, Z and Y, Z form dimers, dimers inactivate one another | X, Z and Y, Z form dimers |
| 1 | 1 | 0 | 0 | 1 | X, Z and Y, Z form dimers, Y/Z dimer precludes X binding Z | X, Z and Y, Z form dimers |
| 1 | 1 | 0 | 1 | 0 | X, Z and Y, Z form dimers, X/Z dimer precludes Y binding Z | X, Z and Y, Z form dimers |
| 1 | 1 | 0 | 1 | 1 | X, Z and Y, Z dimers form | X, Z and Y, Z form dimers |
| 1 | 1 | 1 | 0 | 0 | X, Y forms dimer, X/Y dimer inactivates Z | X, Y and X, Z and Y, Z forms dimers, X/Y/Z trimer may form |
| 1 | 1 | 1 | 0 | 1 | X, Y and X, Z and Y, Z form dimers, Y modifies X, modified X poorly binds Z | X, Y and X, Z, and Y, Z form dimers, X/Y/Z trimer may form |
| 1 | 1 | 1 | 1 | 0 | X, Y and X, Z and Y, Z form dimers, X modifies Y, modified Y poorly binds Z | X, Y, and X, Z and Y, Z, form dimers, X/Y/Z trimer may form |
| 1 | 1 | 1 | 1 | 1 | X, Y and X, Z and Y, Z form dimers, X/Y/Z trimer may form | X, Y and X, Z and Y, Z form dimers, X/Y/Z trimer may form |

Other Embodiments

In an alternative to the above methods, the systems involving two reporter genes described herein may be used to select or screen for proteins that bind to two different protein binding sites. To carry out these screens, two different DNA fragments are inserted upstream of the two reporter genes (for example, a URA3 and a lacZ gene), and expression of each of the genes is assayed in a cell that also contains a gene expressing a candidate binding protein. This candidate binding protein may be expressed in its native state or as a fusion protein joined to an activation domain.

Any of the methods described herein may be used to screen, without limitation, proteins, peptides, or aptamers.

Other embodiments are within the claims.

What is claimed is:

1. A method for detecting the formation of a protein complex, said method comprising:
   (a) providing a first host cell comprising
      (i) a first reporter gene operably linked to a DNA comprising a first protein binding site;
      (ii) a first fusion gene encoding a first fusion protein comprising a first protein covalently bonded to a binding moiety capable of specifically binding to said first protein binding site;
      (iii) a second fusion gene encoding a second fusion protein comprising a second protein covalently bonded to a gene activating moiety; and
      (iv) a third gene comprising a sequence encoding a third protein;
   (b) providing a second host cell comprising
      (i) said first reporter gene;
      (ii) said first fusion gene; and
      (iii) said second fusion gene;
   (c) providing a third host cell comprising
      (i) a second reporter gene operably linked to a DNA comprising a second protein binding site;
      (ii) said second fusion gene; and
      (iii) a third fusion gene encoding said third protein covalently bonded to a binding moiety capable of specifically binding to said second protein binding site;
   (d) measuring expression output of said first reporter gene in said first and said second host cells and said second reporter gene in said third host cell; and
   (e) interpreting the expression output results of step (d), whereby increased output of said first reporter gene in said first host cell relative to the output of said first reporter gene in said second host cell and said second reporter gene in said third host cell indicates that said first, said second, and said third proteins form an oligomeric complex.

2. The method of claim 1, wherein said first binding site and said second binding site are the same.

3. The method of claim 1, wherein said first reporter gene and said second reporter gene are the same.

4. The method of claim 1, wherein said first or said second protein binding site is a tetracycline operator.

5. The method of claim 1, wherein said first or said second reporter gene is URA3 or lacZ.

6. The method of claim 1, wherein said first or said second reporter gene produces a signal that is received and detected by a second cell.

7. The method of claim 1, wherein at least one of said host cells is a yeast cell or a mammalian cell.

8. The method of claim 7, wherein at least one of said host cells is a yeast cell.

9. A method for detecting the formation of a protein complex, said method comprising:
   (a) providing a first host cell comprising
      (i) a first reporter gene operably linked to a DNA comprising a first protein binding site and a second protein binding site;
      (ii) a first fusion gene encoding a first fusion protein comprising a first protein covalently bonded to a binding moiety capable of specifically binding to said first protein binding site;
      (iii) a second fusion gene encoding a second fusion protein comprising a second protein covalently bonded to a binding moiety capable of specifically binding to said second protein binding site; and
      (iv) a third fusion gene encoding a third fusion protein comprising a third protein covalently bonded to a gene activating moiety;
   (b) providing a second host cell comprising
      (i) a second reporter gene operably linked to a DNA comprising said first protein binding site;
      (ii) said first fusion gene; and
      (iii) said third fusion gene;
   (c) providing a third host cell comprising (i) a third reporter gene operably linked to a DNA comprising said second protein binding site;
(ii) said second fusion gene; and
(iii) said third fusion gene;

(d) measuring expression output of said first reporter gene in said first host cell, said second reporter gene in said second host cell, and said third reporter gene in said third host cell; and (e) interpreting the expression output results of step (d), whereby increased output of said first reporter gene in said first host cell relative to the output of said second reporter gene in said second host cell and said third reporter gene in said third host cell indicates that said first, said second, and said third proteins form an oligomeric complex.

10. The method of claim 9, wherein any of said first, said second, or said third reporter genes are the same.

11. The method of claim 9, wherein said second reporter gene or said third reporter gene comprises both said first protein binding site and said second protein binding site.

12. The method of claim 9, wherein at least one of said first or said second protein binding sites is a tetracycline operator.

13. The method of claim 9, wherein at least one of said reporter genes is URA3 or lacZ.

14. The method of claim 9, wherein at least one of said reporter genes produces a signal that is received and detected by a second cell.

15. The method of claim 9, wherein at least one of said host cells is a yeast cell or a mammalian cell.

16. The method of claim 15, wherein at least one of said host cells is a yeast cell.

* * * * *

UNITED STATES PATENT AND TRADEMARK OFFICE
CERTIFICATE OF CORRECTION

PATENT NO. : 6,858,382 B2
DATED : February 22, 2005
INVENTOR(S) : Roger Brent et al.

It is certified that error appears in the above-identified patent and that said Letters Patent is hereby corrected as shown below:

<u>Column 4,</u>
Line 15, replace "(iii)" with -- (ii) --; and
Line 19, replace "(v)" with -- (iii) --.

Signed and Sealed this

Seventh Day of June, 2005

JON W. DUDAS
*Director of the United States Patent and Trademark Office*